(12) United States Patent
Brydon et al.

(10) Patent No.: US 6,213,119 B1
(45) Date of Patent: Apr. 10, 2001

(54) INSPIRATORY DURATION IN CPAP OR ASSISTED RESPIRATION TREATMENT

(75) Inventors: John William Ernest Brydon; Grant Willson, both of New South Wales (AU)

(73) Assignee: ResMed Limited, North Ryde (AU)

(*) Notice: Subject to any disclaimer, the term of this patent is extended or adjusted under 35 U.S.C. 154(b) by 0 days.

(21) Appl. No.: 08/894,190

(22) PCT Filed: Oct. 17, 1996

(86) PCT No.: PCT/AU96/00652

§ 371 Date: Dec. 12, 1997

§ 102(e) Date: Dec. 12, 1997

(87) PCT Pub. No.: WO97/15343

PCT Pub. Date: May 1, 1997

(30) Foreign Application Priority Data

Oct. 23, 1995 (AU) .................................... PN6167

(51) Int. Cl.[7] .......................... A61M 16/00; A62B 7/00; F16K 31/02
(52) U.S. Cl. ................ 128/204.23; 128/204.18; 128/204.21; 128/204.26
(58) Field of Search .............. 128/204.21, 204.23, 128/204.26, 204.18

(56) References Cited

U.S. PATENT DOCUMENTS

| | | | |
|---|---|---|---|
| Re. 35,295 | * 7/1996 | Estes et al. ................. | 128/204.23 |
| Re. 35,339 | 10/1996 | Rapoport . | |
| 2,904,033 | 9/1959 | Shane . | |
| 3,099,985 | 8/1963 | Wilson et al. . | |
| 3,362,404 | * 1/1968 | Beasley ....................... | 128/204.23 |
| 3,502,100 | 3/1970 | Jonson . | |
| 3,559,638 | 2/1971 | Potter . | |
| 3,595,228 | 7/1971 | Simon et al. . | |
| 3,611,801 | 10/1971 | Paine et al. . | |
| 3,726,270 | 4/1973 | Griffis et al. . | |

(List continued on next page.)

FOREIGN PATENT DOCUMENTS

B-59270/90  12/1990  (AU) .
62221/90    3/1991   (AU) .

(List continued on next page.)

OTHER PUBLICATIONS

Derwent: Flowmeter for fluids–has turbine transducer and volumetric sensor for simultaneous calibration.

(List continued on next page.)

John G. Weiss
Assistant Examiner—Joseph F. Weiss, Jr.
(74) Attorney, Agent, or Firm—Pillsbury Madison & Sutro LLP

(57) ABSTRACT

Apparatus for the supply of breathable gas cyclically at an inspiratory pressure and a lower expiratory pressure substantially in synchronism with a patient's respiration. A flow generator coupled to a gas delivery system delivers breathable gas to the patient's airway. A motor controller receives a signal representing respiratory flow. The motor controller sends out a signal to control an electric motor and turbine to generate the desired inspiratory and expiratory pressures. The controller detects transitions between inspiration and expiration via a flow signal to discriminate between the respiratory phases of the patient. A counter counts a first time duration commencing from the last transition to inspiration and whereby if the first time duration elapses before a transition to expiration is detected, the controller initiates the supply of a given expiratory pressure. Furthermore, a second counter counts a second time duration commenced from the last transition to inspiration detected and signals the turbine to supply a given inspiratory pressure until the second time duration has elapsed even if during the second time duration a transition to expiration by the patient has occurred.

17 Claims, 11 Drawing Sheets

U.S. PATENT DOCUMENTS

| | | |
|---|---|---|
| 3,741,208 | 6/1973 | Jonsson et al. . |
| 3,783,893 | 1/1974 | Davison . |
| 3,802,417 | 4/1974 | Lang . |
| 3,817,246 | 6/1974 | Weigl . |
| 3,882,847 | 5/1975 | Jacobs . |
| 3,903,875 | 9/1975 | Hughes . |
| 3,914,899 | 10/1975 | Banner . |
| 3,932,054 | 1/1976 | McKelvey . |
| 3,951,143 * | 4/1976 | Kitrilakis et al. ............... 128/204.23 |
| 3,976,064 * | 8/1976 | Wood et al. ................ 128/204.23 |
| 3,985,467 | 10/1976 | Lefferson . |
| 3,989,037 | 11/1976 | Franetzki . |
| 3,992,598 | 11/1976 | Welsh et al. . |
| 3,995,661 | 12/1976 | Van Fossen . |
| 4,003,377 * | 1/1977 | Dahl ............................. 128/204.23 |
| 4,006,634 | 2/1977 | Billette et al. . |
| 4,057,059 * | 11/1977 | Reid, Jr. et al. .............. 128/204.23 |
| 4,083,245 | 4/1978 | Osborn . |
| 4,109,749 | 8/1978 | Sweet . |
| 4,119,096 | 10/1978 | Drews . |
| 4,206,754 * | 6/1980 | Cox et al. ..................... 128/204.21 |
| 4,211,221 * | 7/1980 | Schwanbom et al. ......... 128/204.26 |
| 4,249,527 | 2/1981 | Ko et al. . |
| 4,301,833 | 11/1981 | Donald, III . |
| 4,312,235 | 1/1982 | Daigle . |
| 4,320,766 | 3/1982 | Alihanka et al. . |
| 4,322,594 | 3/1982 | Brisson . |
| 4,340,045 * | 7/1982 | Manley ......................... 128/204.24 |
| 4,381,788 | 5/1983 | Douglas . |
| 4,387,722 | 6/1983 | Kearns . |
| 4,396,034 | 8/1983 | Cherniak . |
| 4,414,982 | 11/1983 | Durkan . |
| 4,433,693 | 2/1984 | Hochstein . |
| 4,448,058 | 5/1984 | Jaffe et al. . |
| 4,449,525 | 5/1984 | White et al. . |
| 4,481,944 * | 11/1984 | Bunnell ......................... 128/204.18 |
| 4,499,914 | 2/1985 | Schebler . |
| 4,519,399 | 5/1985 | Hori . |
| 4,530,334 | 7/1985 | Pagdin . |
| 4,550,615 | 11/1985 | Grant . |
| 4,550,726 | 11/1985 | McEwen . |
| 4,558,710 | 12/1985 | Eichler . |
| 4,570,631 | 2/1986 | Durkan . |
| 4,576,179 | 3/1986 | Manus et al. . |
| 4,579,114 | 4/1986 | Gray et al. . |
| 4,580,575 | 4/1986 | Birnbaum et al. . |
| 4,592,880 | 6/1986 | Murakami . |
| 4,595,016 | 6/1986 | Fertig et al. . |
| 4,602,644 | 7/1986 | DiBenedetto et al. . |
| 4,630,614 | 12/1986 | Atlas . |
| 4,648,396 | 3/1987 | Raemer . |
| 4,648,407 | 3/1987 | Sackner . |
| 4,655,213 | 4/1987 | Rapoport et al. . |
| 4,677,975 | 7/1987 | Edgar et al. . |
| 4,686,974 | 8/1987 | Sato et al. . |
| 4,686,999 | 8/1987 | Snyder et al. . |
| 4,738,266 | 4/1988 | Thatcher . |
| 4,747,403 * | 5/1988 | Gluck et al. .................. 128/204.21 |
| 4,773,411 | 9/1988 | Downs . |
| 4,777,963 | 10/1988 | McKenna . |
| 4,795,314 | 1/1989 | Prybella et al. . |
| 4,802,485 | 2/1989 | Bowers et al. . |
| 4,803,471 | 2/1989 | Rowland . |
| 4,819,629 | 4/1989 | Jonson . |
| 4,823,788 | 4/1989 | Smith et al. . |
| 4,825,802 | 5/1989 | Le Bec . |
| 4,827,922 | 5/1989 | Champain et al. . |
| 4,838,258 | 6/1989 | Dryden et al. . |
| 4,844,085 | 7/1989 | Gattinoni . |
| 4,856,506 | 8/1989 | Jinotti . |
| 4,860,766 | 8/1989 | Sackner . |
| 4,870,960 | 10/1989 | Hradek . |
| 4,870,963 | 10/1989 | Carter . |
| 4,887,607 | 12/1989 | Beatty . |
| 4,913,401 | 4/1990 | Handke . |
| 4,915,103 | 4/1990 | Visveshwara et al. . |
| 4,928,684 * | 5/1990 | Breitenfelder et al. ......... 128/204.21 |
| 4,938,210 | 7/1990 | Shene . |
| 4,938,212 | 7/1990 | Snook et al. . |
| 4,944,310 | 7/1990 | Sullivan . |
| 4,945,899 * | 8/1990 | Sugiyama et al. ............... 128/204.23 |
| 4,957,107 * | 9/1990 | Sipin ............................. 128/204.21 |
| 4,960,118 | 10/1990 | Pennock . |
| 4,971,065 | 11/1990 | Pearce . |
| 4,972,842 | 11/1990 | Korten et al. . |
| 4,982,738 | 1/1991 | Griebel . |
| 4,986,269 | 1/1991 | Hakkinen . |
| 4,989,599 | 2/1991 | Carter . |
| 5,009,635 | 4/1991 | Scarberry . |
| 5,016,626 * | 5/1991 | Jones ............................. 128/204.26 |
| 5,024,219 | 6/1991 | Dietz . |
| 5,046,491 | 9/1991 | Derrick . |
| 5,048,515 * | 9/1991 | Sanso ............................. 128/204.26 |
| 5,052,400 | 10/1991 | Dietz . |
| 5,063,922 | 11/1991 | Hakkinen . |
| 5,063,938 | 11/1991 | Beck et al. . |
| 5,065,756 | 11/1991 | Rapoport . |
| 5,069,222 | 12/1991 | McDonald, Jr. . |
| 5,090,248 | 2/1992 | Cimmino et al. . |
| 5,099,837 * | 3/1992 | Russel, Sr. et al. ............ 128/204.26 |
| 5,105,354 | 4/1992 | Nishimura . |
| 5,107,830 * | 4/1992 | Younes ........................... 128/204.18 |
| 5,107,831 * | 4/1992 | Halpern et al. ................. 128/204.26 |
| 5,117,819 | 6/1992 | Servidio et al. . |
| 5,129,390 * | 7/1992 | Chopin et al. .................. 128/204.21 |
| 5,134,995 | 8/1992 | Gruenke et al. . |
| 5,148,802 * | 9/1992 | Sanders et al. ................. 128/204.18 |
| 5,150,291 * | 9/1992 | Cummings et al. ............ 364/413.03 |
| 5,161,525 | 11/1992 | Kimm et al. . |
| 5,161,541 | 11/1992 | Bowman et al. . |
| 5,165,398 | 11/1992 | Bird . |
| 5,170,798 | 12/1992 | Riker . |
| 5,174,287 | 12/1992 | Kallok et al. . |
| 5,178,138 | 1/1993 | Walstrom et al. . |
| 5,183,983 | 2/1993 | Knop . |
| 5,190,048 | 3/1993 | Wilkinson . |
| 5,195,528 | 3/1993 | Hok . |
| 5,199,424 | 4/1993 | Sullivan et al. . |
| 5,203,343 | 4/1993 | Axe et al. . |
| 5,230,330 | 7/1993 | Price . |
| 5,231,979 | 8/1993 | Rose et al. . |
| 5,231,983 | 8/1993 | Matson et al. . |
| 5,233,983 | 8/1993 | Markowitz . |
| 5,239,994 * | 8/1993 | Atkins ........................... 128/204.18 |
| 5,239,995 * | 8/1993 | Estes et al. ..................... 128/204.23 |
| 5,245,995 | 9/1993 | Sullivan et al. . |
| 5,259,373 | 11/1993 | Gruenke et al. . |
| 5,271,391 | 12/1993 | Graves . |
| 5,280,784 | 1/1994 | Kohler . |
| 5,293,864 | 3/1994 | McFadden . |
| 5,295,491 | 3/1994 | Gevins . |
| 5,303,698 * | 4/1994 | Tobia et al. ..................... 128/204.21 |
| 5,303,700 * | 4/1994 | Weismann et al. ............. 128/204.23 |
| 5,305,787 | 4/1994 | Thygesen . |
| 5,311,875 | 5/1994 | Stasz . |
| 5,313,937 * | 5/1994 | Zdrojkowski ................... 128/202.22 |
| 5,322,057 | 6/1994 | Raabe et al. . |
| 5,327,899 | 7/1994 | Harris et al. . |
| 5,335,654 | 8/1994 | Rapoport . |
| 5,335,656 | 8/1994 | Bowe et al. . |
| 5,343,878 | 9/1994 | Scarberry et al. . |

| Patent | Date | Inventor | Class |
|---|---|---|---|
| 5,353,788 | 10/1994 | Miles . | |
| 5,360,008 | 11/1994 | Campbell, Jr. . | |
| 5,373,842 * | 12/1994 | Olsson et al. | 128/204.21 |
| 5,388,571 | 2/1995 | Roberts et al. . | |
| 5,394,882 | 3/1995 | Mawhinney . | |
| 5,398,673 | 3/1995 | Lambert . | |
| 5,400,777 * | 3/1995 | Olsson et al. | 128/204.18 |
| 5,404,871 | 4/1995 | Goodman et al. . | |
| 5,433,193 * | 7/1995 | SAnders et al. | 128/204.18 |
| 5,438,980 | 8/1995 | Phillips . | |
| 5,443,061 * | 8/1995 | Champain et al. | 128/204.21 |
| 5,443,075 | 8/1995 | Holscher . | |
| 5,448,996 | 9/1995 | Bellin et al. . | |
| 5,458,137 | 10/1995 | Axe et al. . | |
| 5,479,920 | 1/1996 | Piper et al. . | |
| 5,479,939 | 1/1996 | Ogino . | |
| 5,483,969 | 1/1996 | Testerman et al. . | |
| 5,490,502 | 2/1996 | Rapoport et al. . | |
| 5,492,113 * | 2/1996 | Estes et al. | 128/204.23 |
| 5,503,146 | 4/1996 | Froehlich et al. . | |
| 5,507,282 | 4/1996 | Younes . | |
| 5,509,404 | 4/1996 | Lloyd et al. . | |
| 5,509,414 | 4/1996 | Hok . | |
| 5,513,631 | 5/1996 | McWilliams . | |
| 5,517,983 | 5/1996 | Deighan et al. . | |
| 5,522,382 | 6/1996 | Sullivan et al. . | |
| 5,526,805 | 6/1996 | Luiz et al. . | |
| 5,535,738 | 7/1996 | Estes et al. . | |
| 5,535,739 | 7/1996 | Rapoport et al. . | |
| 5,537,997 | 7/1996 | Mechlenburg et al. . | |
| 5,540,219 | 7/1996 | Mechlenburg et al. . | |
| 5,540,220 * | 7/1996 | Gropper et al. | 128/204.23 |
| 5,540,733 | 7/1996 | Testerman et al. . | |
| 5,546,933 | 8/1996 | Rapoport et al. . | |
| 5,546,952 | 8/1996 | Erickson . | |
| 5,549,106 | 8/1996 | Gruenke et al. . | |
| 5,549,655 | 8/1996 | Erickson . | |
| 5,551,418 * | 9/1996 | Estes et al. | 128/204.23 |
| 5,551,419 | 9/1996 | Froehlich et al. . | |
| 5,558,099 | 9/1996 | Bowman et al. . | |
| 5,567,127 | 10/1996 | Wentz . | |
| 5,570,682 | 11/1996 | Johnson . | |
| 5,577,496 * | 11/1996 | Blackwood et al. | 128/201.25 |
| 5,588,439 | 12/1996 | Hollub . | |
| 5,598,838 | 2/1997 | Servidio et al. . | |
| 5,605,151 | 2/1997 | Lynn . | |
| 5,608,647 | 3/1997 | Rubsamen et al. . | |
| 5,617,846 | 4/1997 | Graetz et al. . | |
| 5,630,411 | 5/1997 | Holscher . | |
| 5,632,269 * | 5/1997 | Zdrojkowski | 128/204.23 |
| 5,633,552 | 5/1997 | Lee et al. . | |
| 5,642,730 | 7/1997 | Baran . | |
| 5,645,053 | 7/1997 | Remmers et al. . | |
| 5,645,054 | 7/1997 | Cotner et al. . | |
| 5,647,351 | 7/1997 | Wesimann et al. . | |
| 5,655,520 | 8/1997 | Howe et al. . | |
| 5,655,522 | 8/1997 | Mechlenburg et al. . | |
| 5,660,171 | 8/1997 | Kimm et al. . | |
| 5,666,946 | 9/1997 | Langenback . | |
| 5,682,878 | 11/1997 | Ogden . | |
| 5,685,296 | 11/1997 | Zdrojkowski et al. . | |
| 5,694,923 * | 12/1997 | Hete et al. | 128/204.18 |
| 5,701,883 * | 12/1997 | Hete et al. | 128/204.26 |
| 5,704,345 * | 1/1998 | Berthon-Jones | 128/204.23 |
| 5,715,812 | 2/1998 | Deighan et al. . | |
| 5,730,121 | 3/1998 | Hawkins et al. . | |
| 5,740,795 * | 4/1998 | Brydon | 128/204.21 |
| 5,794,615 | 8/1998 | Estes . | |
| 5,797,393 * | 8/1998 | Kohl | 128/204.23 |
| 5,797,852 | 8/1998 | Karakasoglu et al. . | |
| 5,803,065 * | 9/1998 | Zdrojkowski et al. | 128/204.23 |
| 5,803,066 | 9/1998 | Rapoport et al. . | |
| 5,823,187 * | 10/1998 | Estes et al. | 128/204.23 |
| 5,845,636 | 12/1998 | Gruenke et al. . | |
| 5,865,173 * | 2/1999 | Froehlich | 128/204.23 |
| 5,901,704 * | 5/1999 | Estes et al. | 128/204.23 |
| 5,904,141 * | 5/1999 | Estes et al. | 128/204.23 |
| 5,931,162 * | 8/1999 | Christian | 128/204.23 |
| 5,970,975 * | 10/1999 | Estes et al. | 128/204.23 |

FOREIGN PATENT DOCUMENTS

| | | |
|---|---|---|
| 76019/91 | 1/1992 | (AU) . |
| 33877/93 | 4/1993 | (AU) . |
| B-59270/90 | 5/1993 | (AU) . |
| 38508/93 | 7/1993 | (AU) . |
| 48748/93 | 9/1993 | (AU) . |
| 52628/93 | 7/1994 | (AU) . |
| 79174/94 | 6/1995 | (AU) . |
| 34471/95 | 2/1996 | (AU) . |
| 40711-95 | 4/1996 | (AU) . |
| 34354/95 | 5/1996 | (AU) . |
| 39130/95 | 6/1996 | (AU) . |
| 3015279 A1 | 10/1981 | (DE) . |
| 3429345 A1 | 6/1985 | (DE) . |
| 34 02 603 A1 | 8/1985 | (DE) . |
| 3537507 A1 | 4/1987 | (DE) . |
| 0 062 166 A2 | 10/1982 | (EP) . |
| 0 066 451 A1 | 12/1982 | (EP) . |
| B1 0 088 761 | 9/1983 | (EP) . |
| 0 164 500 A2 | 3/1985 | (EP) . |
| 0 185 980 | 7/1986 | (EP) . |
| 0 872 643 A2 | 3/1988 | (EP) . |
| 298 367 A2 | 1/1989 | (EP) . |
| 0 452 001 A2 | 3/1990 | (EP) . |
| 0 388 525 A1 | 9/1990 | (EP) . |
| 0 425 092 A1 | 5/1991 | (EP) . |
| 0 461 281 A1 | 12/1991 | (EP) . |
| 0 481 459 A1 | 4/1992 | (EP) . |
| 481 459 A1 | 4/1992 | (EP) . |
| 0514 744 | 11/1992 | (EP) . |
| 0549299 A2 | 6/1993 | (EP) . |
| 606 687 A2 | 7/1994 | (EP) . |
| 0 714 670 A2 | 12/1994 | (EP) . |
| 0651971 A1 | 5/1995 | (EP) . |
| 0 656 216 A2 | 6/1995 | (EP) . |
| 0 661 071 A1 | 7/1995 | (EP) . |
| 178 925 A2 | 4/1996 | (EP) . |
| 0 709 107 A1 | 5/1996 | (EP) . |
| 0 714 670 A2 | 6/1996 | (EP) . |
| 0 765 631 A2 | 4/1997 | (EP) . |
| 0 788 805 A2 | 8/1997 | (EP) . |
| 2 672 221 | 8/1992 | (FR) . |
| 2682042 A1 | 4/1993 | (FR) . |
| 1432572 | 4/1976 | (GB) . |
| 1 444 053 | 7/1976 | (GB) . |
| 1583273 | 1/1981 | (GB) . |
| 2 077 444 | 12/1981 | (GB) . |
| 2 147 506 | 5/1985 | (GB) . |
| 2 164 569 | 3/1986 | (GB) . |
| 2 166 871 | 5/1986 | (GB) . |
| 2 205 167 | 11/1988 | (GB) . |
| 2 221 302 | 1/1990 | (GB) . |
| 2 254 700 | 10/1992 | (GB) . |
| 2 261 290 | 5/1993 | (GB) . |
| 2 271 811 | 4/1994 | (GB) . |
| 2 294 400 | 5/1996 | (GB) . |
| 54-104369 | 8/1979 | (JP) . |
| 60-212607 | 10/1985 | (JP) . |
| 62-103297 | 4/1987 | (JP) . |
| 63-275352A | 5/1987 | (JP) . |
| 63-275352 | 11/1988 | (JP) . |
| 2-173397 | 12/1988 | (JP) . |

| | | |
|---|---|---|
| 4-70516 | 3/1992 | (JP). |
| 06249741 | 9/1994 | (JP). |
| 6-249742 | 9/1994 | (JP). |
| 07280609 | 10/1995 | (JP). |
| 8019610 | 1/1996 | (JP). |
| 1710064 A1 | 2/1992 | (SE). |
| 467041 | 5/1992 | (SE). |
| WO 80/01044 | 5/1980 | (WO). |
| WO 82/03326 | 10/1982 | (WO). |
| WO 82/03548 | 10/1982 | (WO). |
| WO 86/05965 | 10/1986 | (WO). |
| WO 86/06969 | 12/1986 | (WO). |
| WO 87/02577 | 5/1987 | (WO). |
| WO 89/09565 | 10/1988 | (WO). |
| WO 88/10108 | 12/1988 | (WO). |
| WO 90/09146 | 8/1990 | (WO). |
| WO 90/14121 | 11/1990 | (WO). |
| WO 91/12051 | 8/1991 | (WO). |
| WO 91/19456 | 12/1991 | (WO). |
| WO 92/11054 | 7/1992 | (WO). |
| WO 92/15353 | 9/1992 | (WO). |
| WO 92/22244 | 12/1992 | (WO). |
| WO 93/08857 | 5/1993 | (WO). |
| WO 93/09834 | 5/1993 | (WO). |
| WO 93/21982 | 11/1993 | (WO). |
| WO 93/24169 | 12/1993 | (WO). |
| WO 94/04071 | 3/1994 | (WO). |
| WO 94/16759 | 8/1994 | (WO). |
| WO 94/20018 | 9/1994 | (WO). |
| WO 94/20051 | 9/1994 | (WO). |
| WO 94/22517 | 10/1994 | (WO). |
| WO 94/23780 | 10/1994 | (WO). |
| WO 95/32016 | 11/1995 | (WO). |
| WO 95/34917 | 12/1995 | (WO). |
| WO 96/16688 | 6/1996 | (WO). |
| WO 96/32055 | 10/1996 | (WO). |
| WO 96/36279 | 11/1996 | (WO). |
| WO 96/40337 | 12/1996 | (WO). |
| WO 96/41571 | 12/1996 | (WO). |
| WO 97/02064 | 1/1997 | (WO). |
| WO 97/05824 | 2/1997 | (WO). |
| WO 97/10019 | 3/1997 | (WO). |
| WO 97/10868 | 3/1997 | (WO). |
| WO 97/14354 | 4/1997 | (WO). |
| WO 97/15343 | 5/1997 | (WO). |
| WO 97/18752 | 5/1997 | (WO). |
| WO 97/20499 | 6/1997 | (WO). |
| WO 97/22377 | 6/1997 | (WO). |
| WO 97/28838 | 8/1997 | (WO). |
| WO 97/41812 | 11/1997 | (WO). |
| WO 98/06449 | 2/1998 | (WO). |
| WO 98/25662 | 6/1998 | (WO). |
| WO 98/33433 | 8/1998 | (WO). |
| WO 98/35715 | 8/1998 | (WO). |
| WO 98/36245 | 8/1998 | (WO). |
| WO 98/36338 | 8/1998 | (WO). |
| WO 98/47554 | 10/1998 | (WO). |
| WO 98/52467 | 11/1998 | (WO). |
| WO 98/57691 | 12/1998 | (WO). |

OTHER PUBLICATIONS

Mark Kantrowitz, Erik Horskotte and Cliff Joslyn; "Answers to Frequently Asked Questions about Fuzzy Logic and Fuzzy Expert Systems" Version 1.24 last Modified 20 2 96.

New! Breas PV 100 CPAP First Class Quality and Function. At the right Price; 07/04/98, pp 1–2.

PV 101 Bi Level CPAP and PV 102 Bi–Level Time; pp 1–3.

Prodigy Medical Supplies Co. Ltd.; CPAP.

Puritan Bennett; Companion 318 Nasal CPAP Systems; 5/93.

Nellcor Puritan Bennett; Announcing the Goodnight 314 and GoodKnight 318 Nasal CPAP Systems.

Puritan Bennett; Clean, Quiet, and Comfortable . . . The Companion's 515 Nasal CPAP Systems; 6/88.

DeVilbiss Night Guard Nasal CPAP for the Treatment of Obstructive Sleep Apnea.

Sunrise; DeVilbiss Horizon LT 8001 Nasal CPAP Therapy Small in Size, big on features; 8/97.

Devilbiss; Revitalizer Soft Start; The Facts for Themselves, 1992.

Tranquility; Performance CPAP Advantage.

Healthdyne International; Tranquility Plus.

Respironics Inc.; Respironics' Solo CPAP System Provides Simplified OSA Therapy at an Outstanding value; 9/19/96.

Respironics Inc.; The First Family of OSA Therapy; 1991.

Fisher & Paykel Healthcare; HC200 Series Nasal CPAP Blower & Heated Humidifier.

Pierre Medical; Morphee Plus appareil de traitment des apneas du sommeil manuel d'utilisation.

Weinmann:Hamburg; Somnotron nCPAP–Great WM 2300, 11/91.

Puritan Bennett; 515a Part of Our Blueprint for the Future; 03/90.

Puritan Bennett; Companion 320 I/E Bi–Level Respiratory System; 4/93.

ResMed; Sullivan VPAP II & II ST.

ResMed; The Sullivan V Family of CPAP Systems; 1996.

ResMed; The AutoSet Portable II; 1997.

ResMed; Sullivan Nasal CPAP System.

ResMed; The Sullivan IIID; 1995.

ResMed; The Sullivan Comfort; 1996.

DeVilbiss a Division of Sunrise Medical; Expand your Horizons With The Horizons; 1995.

Healthdyne Technologies; Home Health Care Dealer; The Journal of Home Medical Equipment and Services/Supplier; Nov. and Dec. 1997.

Healthdyne International; Tranquility Quest, The Compact CPAP for Greater patient comfort.

AirStep; Medical Products . . . Stand the Test of Time.

MAP Medical Progress for Physician und Patient; The Gentle Theray for Sleep–Related Breathing Disorders.

Taema; Ventilation CP 90.

DPAP; Breath, by breath, by breath.

Lifecare; Smallest. Quietest. Smartest.

Lifecare; Quiet CPAP System for Maximum Compliance; 1991.

Lifecare; Software Nasal Mask, Custom Nasal Masks; 1991.

Nidek Medical; Silenzio.

Weinmann; Just to Fell Well, Sensitive Sleep Apnea Therapy with Somnotron 3 and Somno–Mask System.

Respironics Inc.; Aria CPAP System; 1993.

Respironics Inc.; SleepEasy III A New Dawn in Patient Compliance.

Respironics Inc.; Muliple Choice REMstar Choice Nasal CPAP System.

MaxII nCPAP and Moritz II Bi–Level Brochure.

* cited by examiner

*Primary Examiner—*

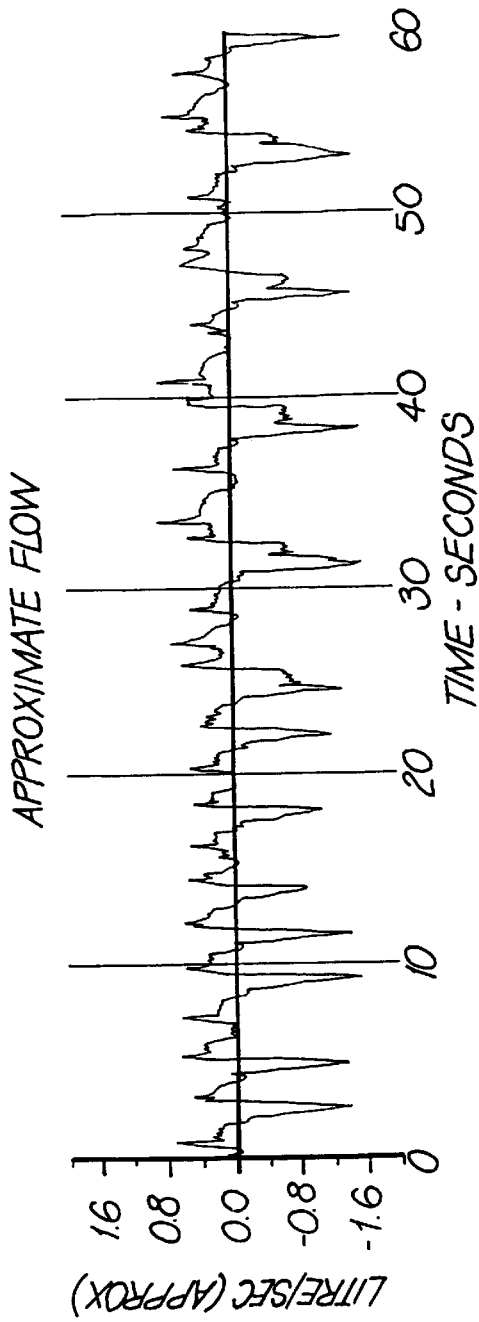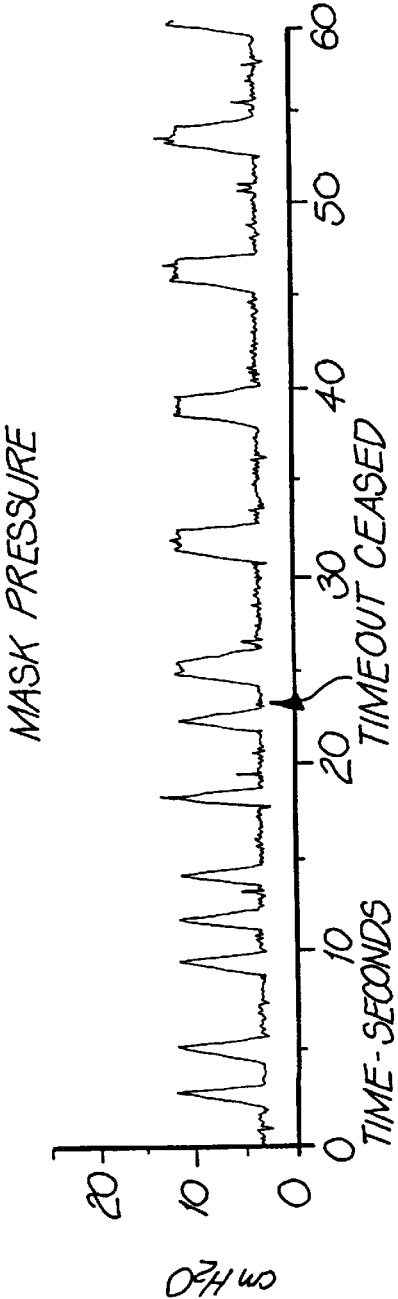

INSPIRATORY DURATION IN CPAP OR ASSISTED RESPIRATION TREATMENT

FIELD OF THE INVENTION

This invention relates to the selection and/or automatic control of IPAP duration during CPAP or assisted respiration treatment. In preferred non-exclusive forms, it relates to the selection of a variable maximum IPAP duration, a variable minimum IPAP duration and the automatic adjustment of a variable IPAP duration, or combinations of these.

In this specification references to "transitions between inspiration and expiration" are to be understood as transitions both from inspiration to expiration and from expiration to inspiration.

BACKGROUND OF THE INVENTION

The administration of non-invasive CPAP (Continuous Positive Airway Pressure) is an effective way of treating patients who suffer from OSA (Obstructive Sleep Apnea) and upper airway resistance syndrome. CPAP treatment effectively acts as a pneumatic splint of the patient's upper airway. Common to all forms of non-invasive CPAP apparatus is a nose, mouth or face mask which is fitted to a patient and connected via a flexible air delivery tube/conduit. The flow generator includes an electric motor driving a turbine to supply air or breathable gas for the administration of CPAP treatment to the patient during sleep. The positive air pressures supplied at the entrance to the patient's airway typically is in the range 2–20 cm $H_2O$.

In bilevel CPAP, the pressure of the delivered air or breathable gas is ideally switched between two levels coinciding (in synchronism) with patient breathing. The pressure required to maintain adequate airway patency is typically substantially higher in inspiration than in expiration. Further, the pressure level required during inspiration is approximately equal to the single fixed pressure level used in CPAP therapy. This observation permits the administration of a lower pressure (referred to as EPAP) in expiration, and a higher pressure (referred to as IPAP) during inspiration. Therefore, the mean pressure delivered to the patient is reduced compared with CPAP therapy, leading to increased comfort and potential compliance. In some instances bilevel CPAP may also be used to provide respiratory assistance or ventilation. Much of the practical difficulty in designing CPAP apparatus is the accurate detection of the transition between inspiration to expiration so that synchronism with respiration is maintained.

When bilevel CPAP treatment is employed using only a nose mask, for some patients the higher IPAP pressure can introduce a mouth leak by which air entering the nose escapes via the mouth. The presence of a mouth leak during IPAP makes it difficult for the CPAP apparatus to accurately detect when the patient exhales. The IPAP pressure therefore may erroneously be maintained during expiration, thereby increasing the work of breathing, possibly leading to an arousal from sleep.

One method of circumventing the problem of mouth-leak is to use a full face mask or a combined nose/mouth mask; however this may lead to discomfort for some patients and effectively sealing the mask is difficult.

An alternate manner of minimising the effect of mouth-leak is to limit the maximum time for which the CPAP apparatus can remain in the IPAP state. With an appropriate limit on the duration of the IPAP time, the machine eventually 'times-out' and reverts to EPAP treatment pressure if it is unable to detect, as a result of a leak, that the patient has exhaled. When the patient next inhales, the CPAP apparatus detects this occurrence and reverts to the IPAP treatment pressure.

In all known bilevel CPAP apparatus the IPAP time-out is of a fixed duration, typically three seconds, which is longer than the usual maximum inspiratory time. From clinical trials conducted by the present inventors, it has become apparent that problems still arise, as it is possible for a patient to take a number of breaths before the time-out occurs. The patient must therefore still breath against the IPAP pressure, so the work of breathing is increased. The benefits of the delivered therapy are therefore diminished and, in some cases, the device may act to the patient's detriment.

The present invention is directed to overcoming or at least ameliorating one or more of the above-mentioned disadvantages.

DISCLOSURE OF THE INVENTION

In one broad form, the invention discloses a controller for a flow generator to supply breathable gas cyclically at an inspiration pressure and at a lower expiration pressure substantially in synchronism with the patient's respiration, the controller comprising:

data processing means for receiving an input respiratory flow signal and for detecting transitions between inspiration and expiration from said flow signal to discriminate between patient inspiration and expiration, and for outputting a control signal to the flow generator to set the inspiratory pressure and the expiratory pressure, and timer means operable to select a time duration commencing from the last transition to inspiration whereby if said first time inspiratory duration elapses before the data processing means detects a transition to expiration by the patient, the output signal from the data processing means causes the flow generator to supply said expiration pressure.

The time duration can be user adjustable. In another form, there is provided a second time duration commencing from the last transition to inspiration corresponding to the data processing means forcing said flow generator to supply said inspiration pressure until said second time duration elapses even if during said second time duration there is a transition to expiration by the patient. Furthermore, data processing means can periodically update said first time duration based on one or more subsequent respiratory transitions to expiration and whether the first time duration elapses before one or more of said subsequent transitions occur, to converge the elapse of said first time duration with said subsequent transitions to expiration.

The invention further discloses CPAP or assisted respiration apparatus comprising a controller as described above, a flow generator coupled to the controller for supplying breathable gas to a gas delivery system providing the breathable gas to the patient's airway, and a flow sensor located in said gas delivery system.

The invention further discloses a method for controlling the supply of breathable gas to a patient cyclically at an inspiration pressure and at a lower expiration pressure substantially in synchronism with the patient's respiration, the method comprising the steps of:

(a) measuring patient respiratory flow;
(b) detecting transitions between inspiration and expiration from said respiratory flow to discriminate between patient inspiration and expiration;

(c) controlling the pressure of gas to be at the inspiration pressure during patient inspiration and at the expiratory pressure during patient expiration; and (d) prescribing a first time duration commencing from the last transition to inspiration by the patient, and if a said duration elapses before patient transition to expiration, causing the pressure of gas to be at the expiratory pressure.

Preferably, the method comprises the further step of:

(e) prescribing a second time duration commencing from the last transition to inspiration, and causing the pressure of gas to be at the inspiratory pressure until the elapse of said second time duration even if there is a transition to expiration by the patient during the second time duration.

Yet further, there can be the further step of:

(f) updating said first time duration based on one or more previous respiratory transitions to expiration and whether the first time duration elapses before one or more of said previous transitions occur to converge the elapse of said first time duration with said previous transitions to expiration.

The provision of a variable maximum inspiratory treatment pressure duration is advantageous in maintaining synchronism between CPAP apparatus and a patient's breathing, thereby maintaining efficacy of the treatment and ensuring that the workload of breathing is not increased. This is particularly so for those patients who exhibit mouth-leak during IPAP.

For a small percentage of patients receiving CPAP treatment, for example those with REM hypoventilation, only small inspiratory effort is made. Under the bilevel regime, it is conventionally the case that because of the small inspiratory effort the CPAP apparatus will make a transition to EPAP while the patient still is inspiring. Thus an advantage of a variable minimum inspiratory duration is that the patient does not have to make a sustained respiratory effort in order that the IPAP pressure be maintained. Adequate ventilation or respiratory assistance therefore can be assured. Further, the ability to vary the minimum IPAP duration enables the physician to match the therapy to the patient's normal breathing whilst asleep.

An advantage of the automatic adjustment of the maximum IPAP duration is that variations in a patient's breathing, which might occur overnight, seasonally or with disease progression, can be accounted for and near synchronism with the patient's respiration maintained.

BRIEF DESCRIPTION OF THE DRAWINGS

Embodiments of the invention now will be described with reference to the accompanying drawings, in which:

FIGS. 3a to 9b show clinical data of respiratory flow and bi-level CPAP treatment pressure for a number of patients with and without maximum IPAP duration;

DESCRIPTION OF PREFERRED EMBODIMENTS AND BEST MODE

Figure 1:
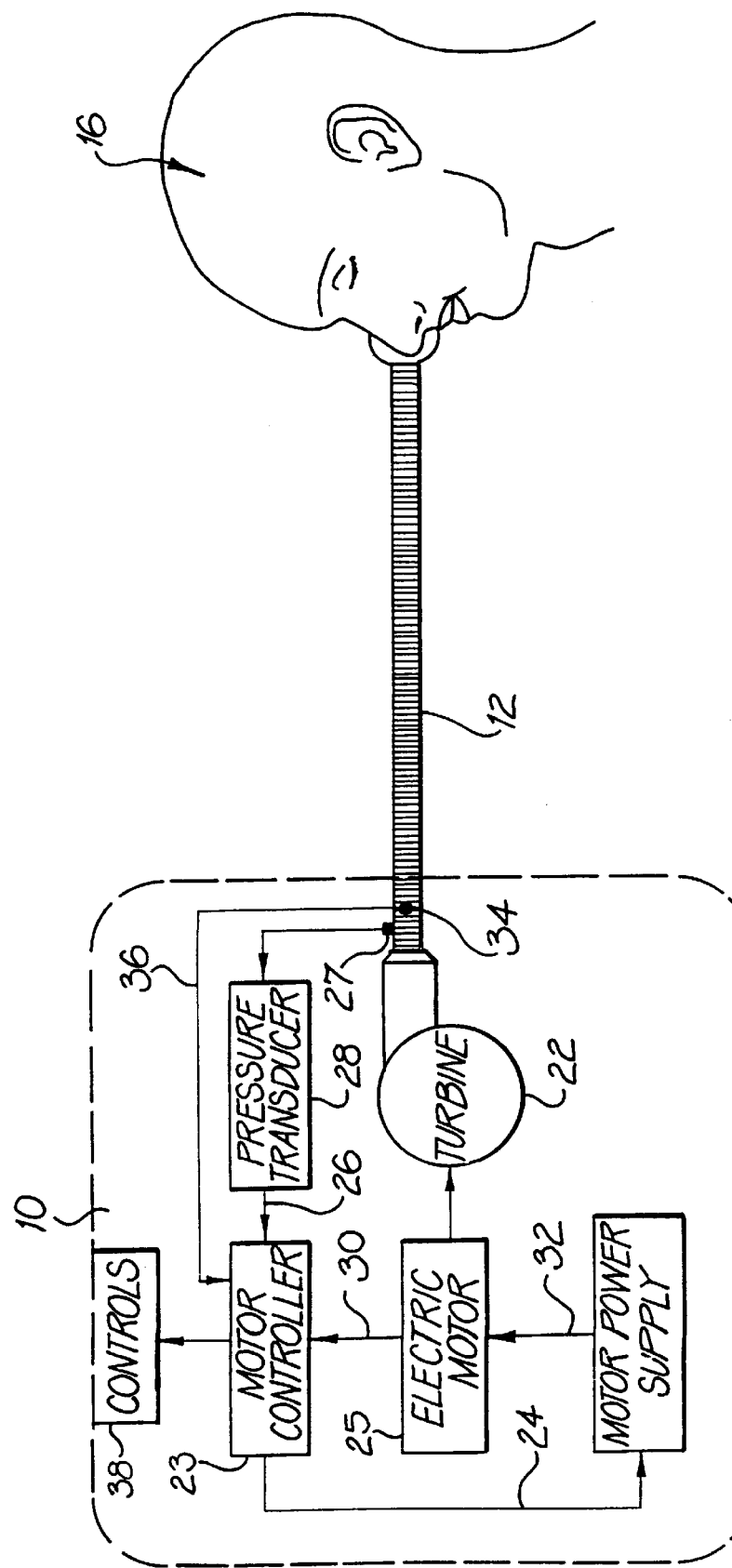
FIG. 1 is a schematic block diagram of bilevel CPAP apparatus.

The embodiments described relate to CPAP apparatus and treatment, however, the invention is to be understood as being equally applicable to assisted respiration devices. Referring then to FIG. 1, the CPAP apparatus comprises a flow generator 10 coupled by a flexible delivery tube or conduit 12 to, in this case, a nose mask 14 worn by a patient 16. The flow generator 10 broadly comprises an electric motor 18 that is powered by a motor power supply 20. In turn, the electric motor 18 has mechanical coupling with a turbine 22 that outputs either air or breathable gas at a pressure elevated above atmospheric pressure to the delivery tube 12. The output delivery pressure from the turbine 22 is governed by the rotational speed of the electric motor 18, the speed therefore being the controlled variable relative to the desired CPAP treatment pressure. The motor 18 speed is controlled by the motor controller 23 which effects changes in motor speed by means of a control signal on control line 24 provided to the motor power supply 20. Thus motor speed is controlled by means of varying the motor power supply 20.

The motor controller 23 receives an electrical signal on control line 26 representative of, in this case, delivery pressure from the turbine 22 as measured by the pressure transducer 28 which is connected via a sensing line 29 to a sensing port 27 proximate to the turbine outlet. The sensing of delivery pressure is important in maintaining regulation of treatment pressure.

An inline flow transducer 34 also is provided near the outlet to the turbine 22, and supplies a flow signal to the motor controller 23 on line 36. The function of the flow sensor will be presently described.

In one preferred form, the motor 25 driving the turbine 22 can be a PAPST™ ECA 27-11 brushless DC motor. Being a DC motor, its speed is directly proportional to the armature voltage. The particular motor described has integral Hall-effect sensors, thus providing a measure of motor angular rotational speed required for speed (and hence delivery pressure) regulation, that signal being output from the motor 18 to the motor controller 22 on control line 30.

The pressure transducer 28 can be such as a Motorola™ MPX 2010DP type. The flow transducer can be such as a Micro Switch™ AWM2200V type. The motor controller 23 can be implemented by any commercially available microprocessor, although one preferred form is the 8-bit Motorola™ MC68HC805B6 micro-controller.

As briefly described above, bilevel CPAP treatment controls the pressure of the air or breathable gas supplied to the entrance of the patient's airway as a higher inspiratory pressure in phase with the patient's inspiration, and a lower expiratory pressure in phase with the patient's expiration. Typical differences between the IPAP and EPAP treatment pressures are 6–12 cm $H_2O$. In order to implement bilevel CPAP treatment, it is necessary to detect the transitions between patient inspiration and expiration so that the IPAP and EPAP treatment pressures can be in synchronism with the respective phases of respiration. Such transitions are detected by means of the flow transducer 34, in that a zero crossing or threshold value can be discriminated as a trigger to a transition event. In this regard, reference can be had to the bilevel CPAP apparatus commercially available from the present applicant and sold under the trade mark "VPAP".

FIG. 1 also shows a set of controls 38, which can be in the form of potentiometers, pushbuttons or the like for manual adjustment of parameters relating to IPAP duration. The controls may be located within the casing of the CPAP apparatus so as only to be accessed by a physician or trained technician, or in the alternative they may be generally accessed from outside of the casing for free manipulation by a patient directly or by a physician or technician.

Figure 2:
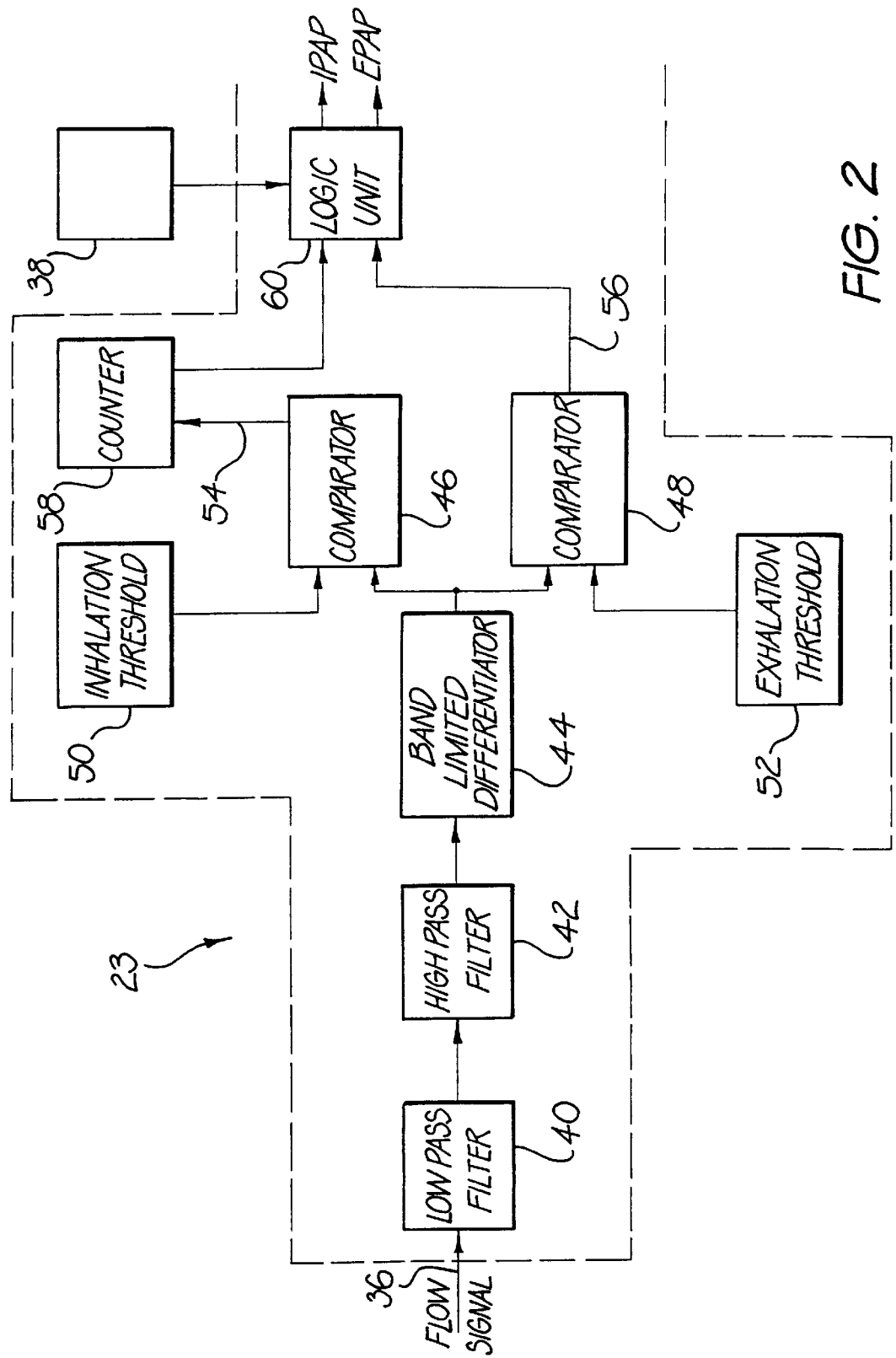
FIG. 2 is a functional block diagram of a respiration detection circuit incorporating variable maximum IPAP duration.

FIG. 2 is a functional block diagram that represents logic elements, typically implemented by one or more computer programs, within the motor controller 23. The signal representative of flow on line 36 is input to a low pass filter 40 typically having an upper limiting frequency of 20 Hz and intended to remove noise in the flow signal. The output of the low pass filter is supplied to a high pass filter 42, typically having a lower limiting frequency of 0.5 Hz that removes non-respiratory components of the signal. The output of the high pass filter then is supplied to a band-limited differentiator 44, the output of which thus represents the time rate of change of the flow signal. The output of the differentiator 44 is provided to separate comparators 46,48. Associated with each of the comparators 46,48 is a respective threshold reference unit 50,52. The comparators and respective threshold reference units relate to the separate detection of inspiration and expiration so as to control the supplying of IPAP and EPAP treatment pressure to a patient.

The comparator 46 thus compares the time differentiated and filtered flow signal with a threshold reference from the threshold reference unit 50, and when the threshold is exceeded (in the negative sense) an "inhalation detection signal" 54 is generated. That is, the occurrence of negative gradient in the flow signal represents a transition to inspiration. Conversely, a positive gradient in the flow signal represents a transition to expiration. In that case, the reference threshold supplied by the threshold reference unit 52 to the comparator 48 is positive, with the output 56 from the comparator 48 representing an "exhalation detection signal" being provided to a logic unit 60.

The inhalation detection signal 54 is passed to a counter 58, which is in the nature of a resettable timer that determines the duration for which the inhalation detection signal 54 has been active. The output of the counter is provided to the logic unit 60.

The controls 38 also provide an input to the logic unit 60, by which the maximum allowable IPAP duration (time-out) can be set. The duration/time-out typically will be set to the patient's prevailing inspiratory time. In this way, the logic unit 60 watches the state of the counter 58 following commencement of a patient inspiration, and if the counter does not reset (for reason of a transition to expiration) before the elapse of the maximum duration/time-out set by the controls 38, then the logic unit 60 forces a change to the EPAP state. An output of the logic unit 60 therefore is an EPAP control signal that has control over the state of operation of the CPAP apparatus as to provision of either EPAP treatment pressure. Conversely, the other output to the logic unit 60 is an IPAP control signal. Selection, control and regulation of the respective EPAP and IPAP treatment pressures is performed by other logic units of the motor controller 23 in the conventional manner.

In all of FIGS. 3a–9b the clinical traces denominated "a" represent approximate respiratory flow rate. The convention adopted is that negative flow equates to inspiration, and as follows, positive flow relates to expiration. The traces denominated "b" represent CPAP treatment pressure. The treatment is in the nature of bi-level CPAP, with the higher treatment pressure intended to correspond with patient inspiration, and the lower treatment pressure intended to correspond with patient expiration. The duration of the inspiratory and expiratory portions of the CPAP treatment are as provided by bi-level CPAP apparatus, such as the present applicant's "VPAP" apparatus, that seek to maintain synchrony with transitions in the patient's respiration. Thus the respective duration of the inspiratory and expiratory portions of the CPAP treatment can be seen to vary in time.

Figure 3A:
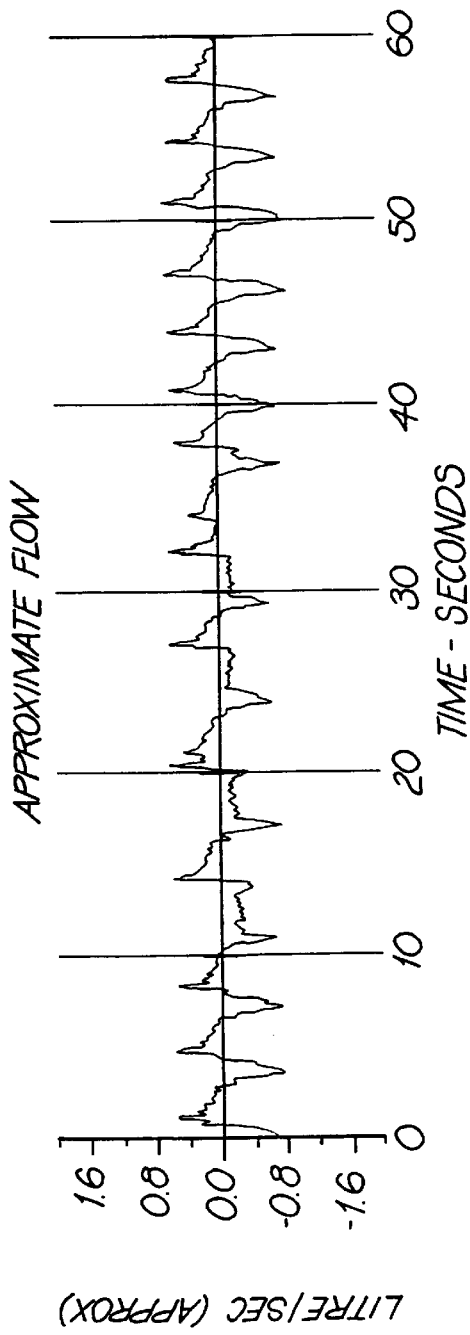
Figure 3B:
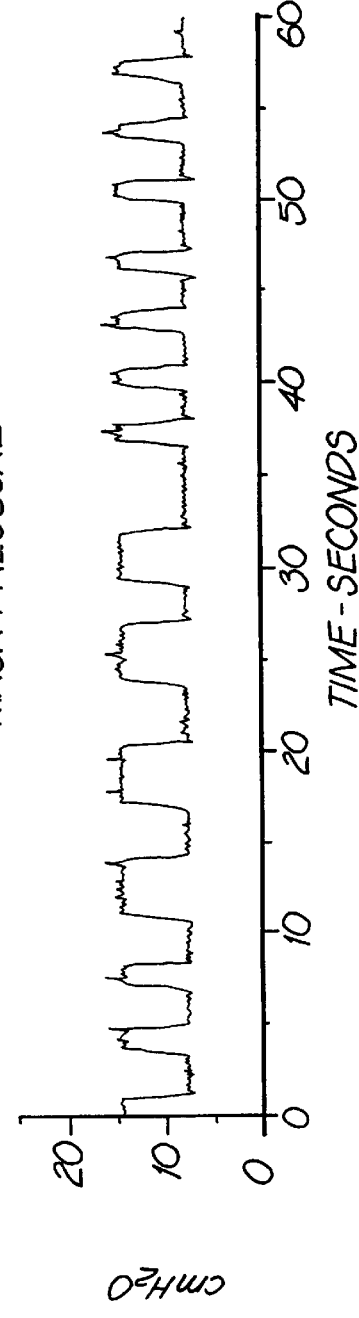
Figure 4A:
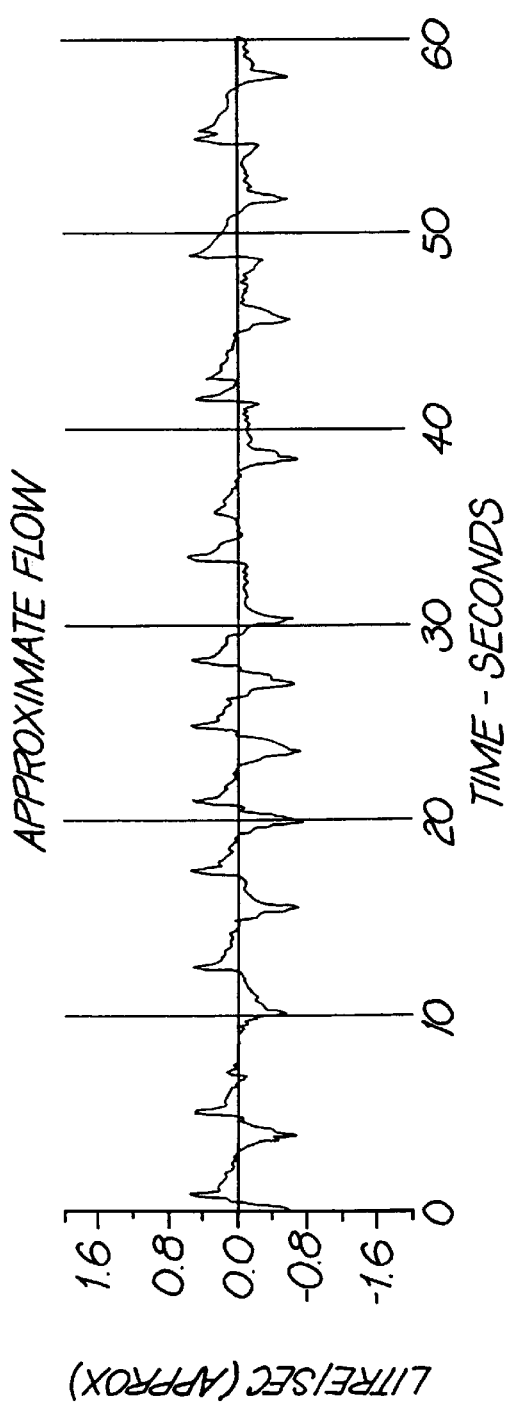
Figure 4B:
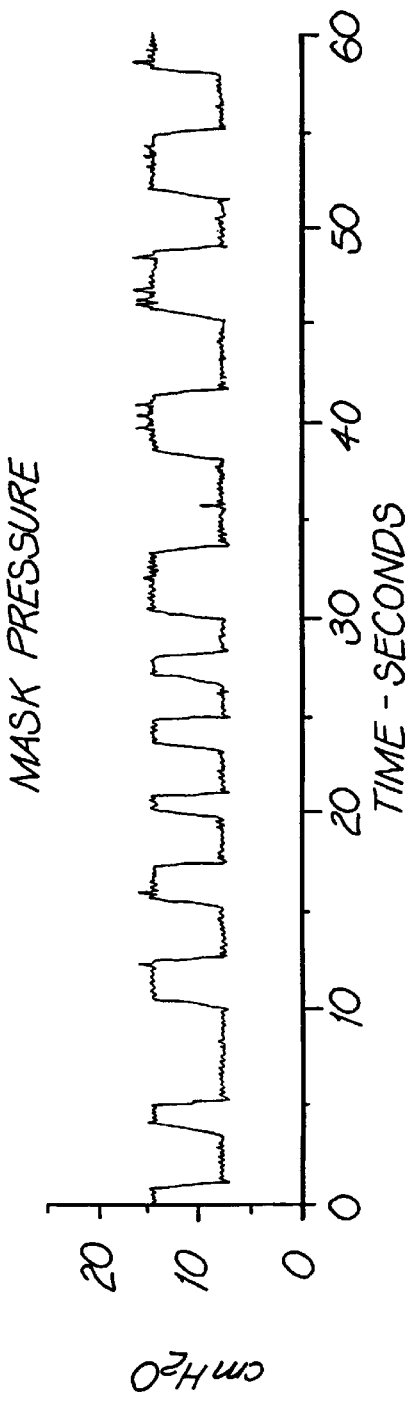

The patient from whom the respiratory traces shown in FIGS. 3a and 3b were made suffers from OSA and REM (Rapid Eye Movement) hypoventilation. A study of the respective flow and pressure traces reveals asynchrony following the third, fourth, fifth and sixth transitions from IPAP to EPAP. This is a pattern that is due essentially to mouth leak, and can at times result in patient arousal. Such asynchrony can, in some patients, lead to ineffective ventilation and may increase the work of breathing.

Figure 5A:
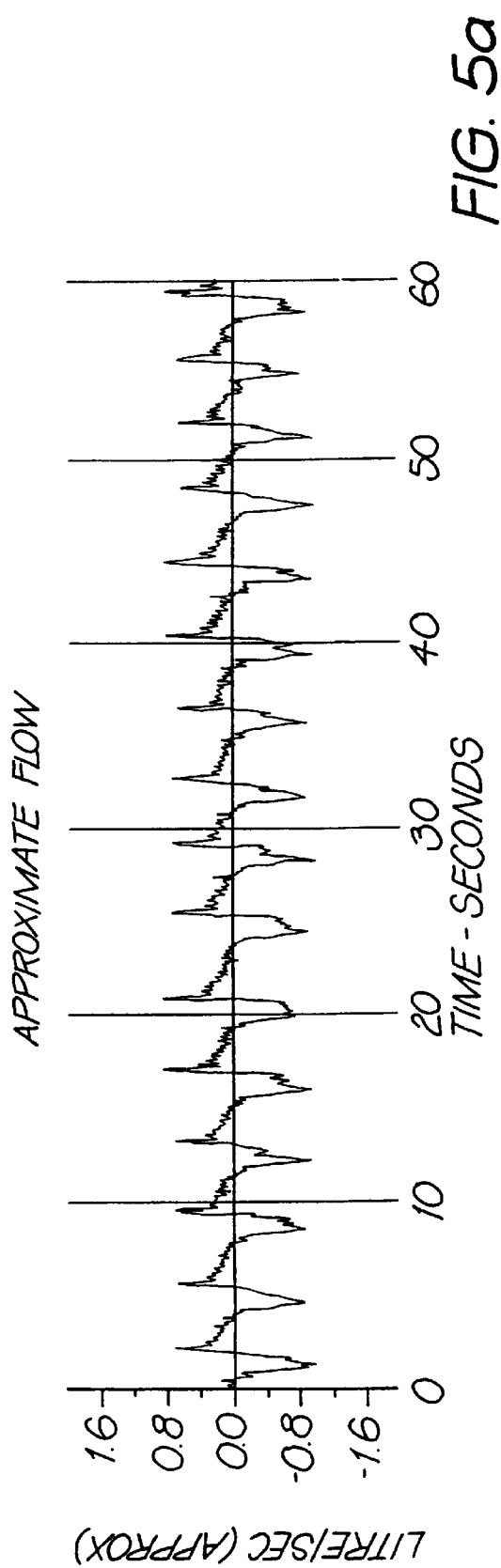
Figure 5B:
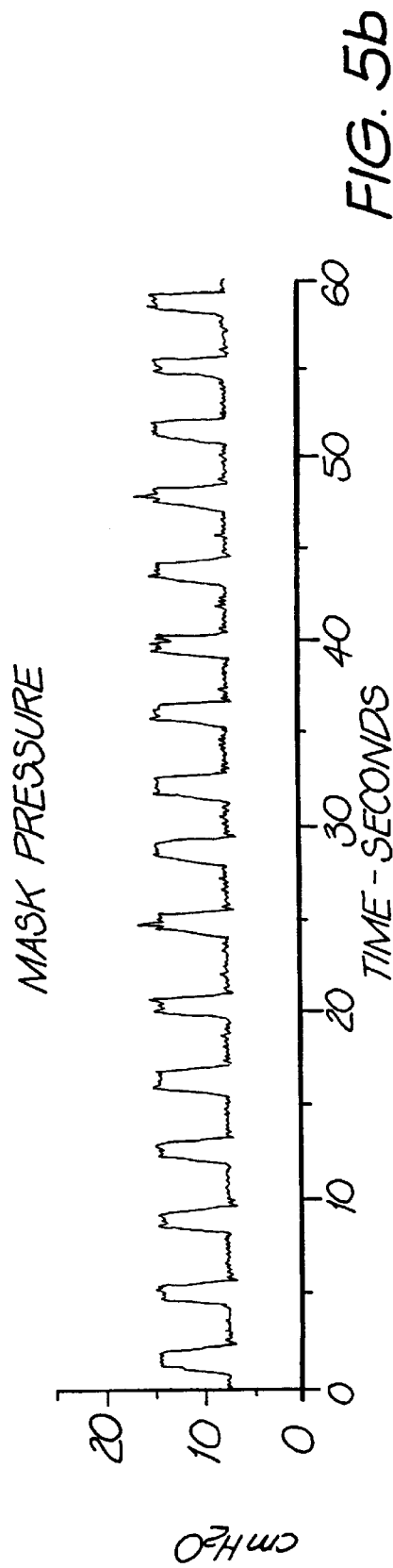
Figure 6A:
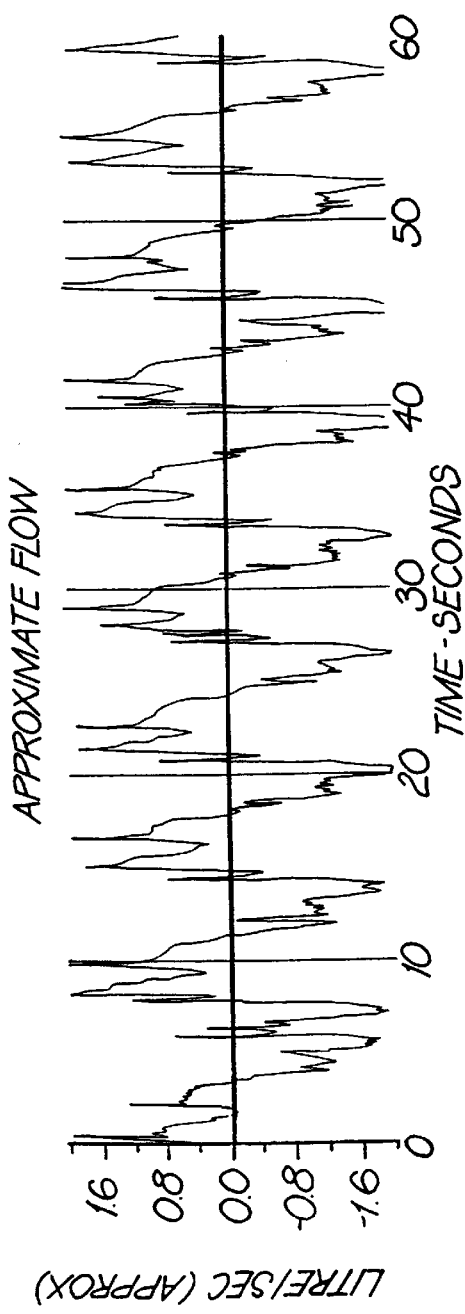
Figure 6B:
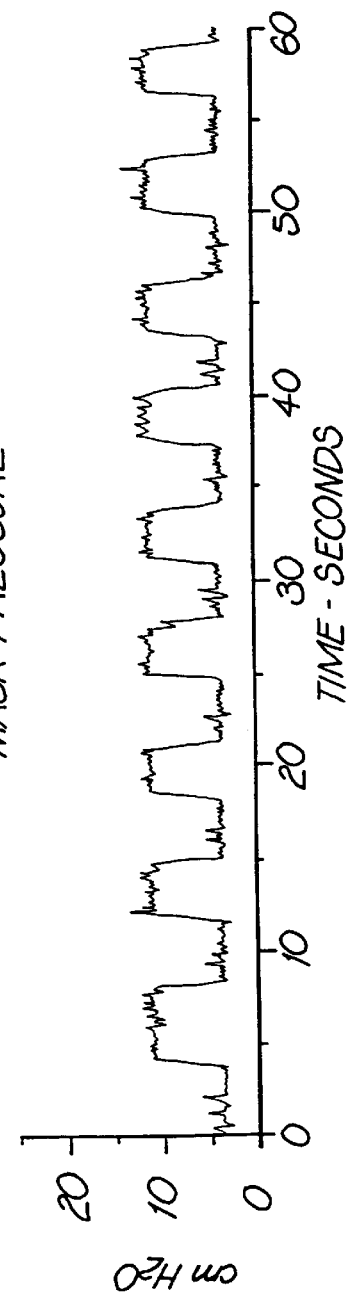

The traces shown in FIGS. 5a and 5b are for the same patient as for FIGS. 3a–4b, however with maximum IPAP duration being practiced. As can be noted, there is a dramatic improvement in the synchronism of the patient's respiration with treatment pressures.

Figure 7A:
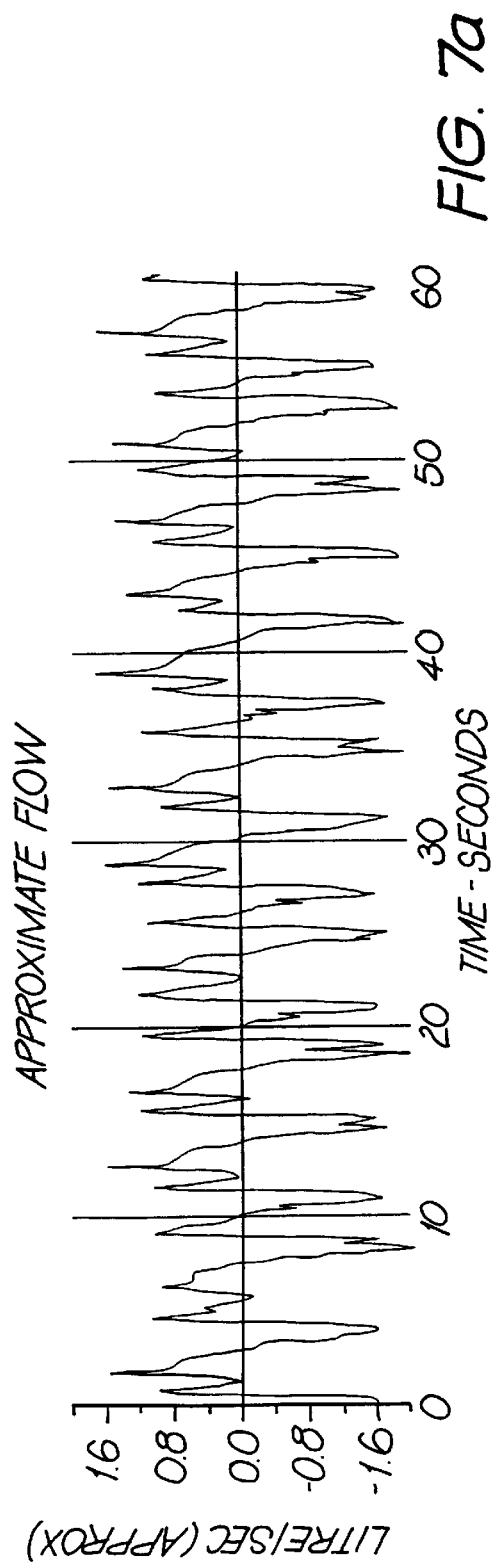
Figure 7B:
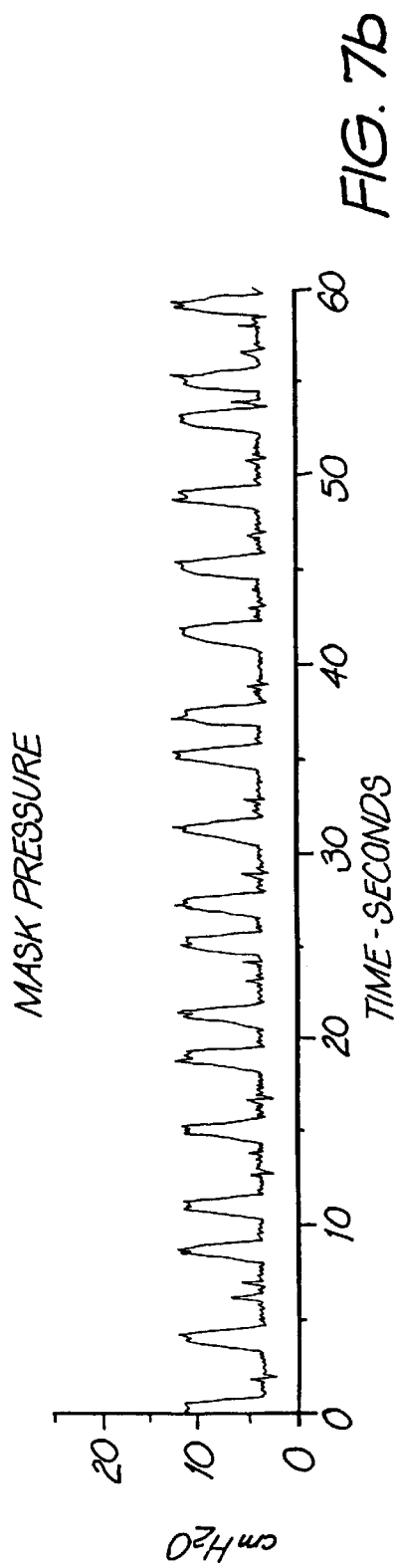

The traces shown in FIGS. 6a–7b relate to a patient having severe lung disease. As can be seen from FIGS. 6a and 6b, the duration of and time of transition between the IPAP and EPAP treatment pressures are only poorly in synchronism with the patient's respiration. FIGS. 7a and 7b show an improved synchronism where maximum IPAP duration is in effect.

Figure 9A:
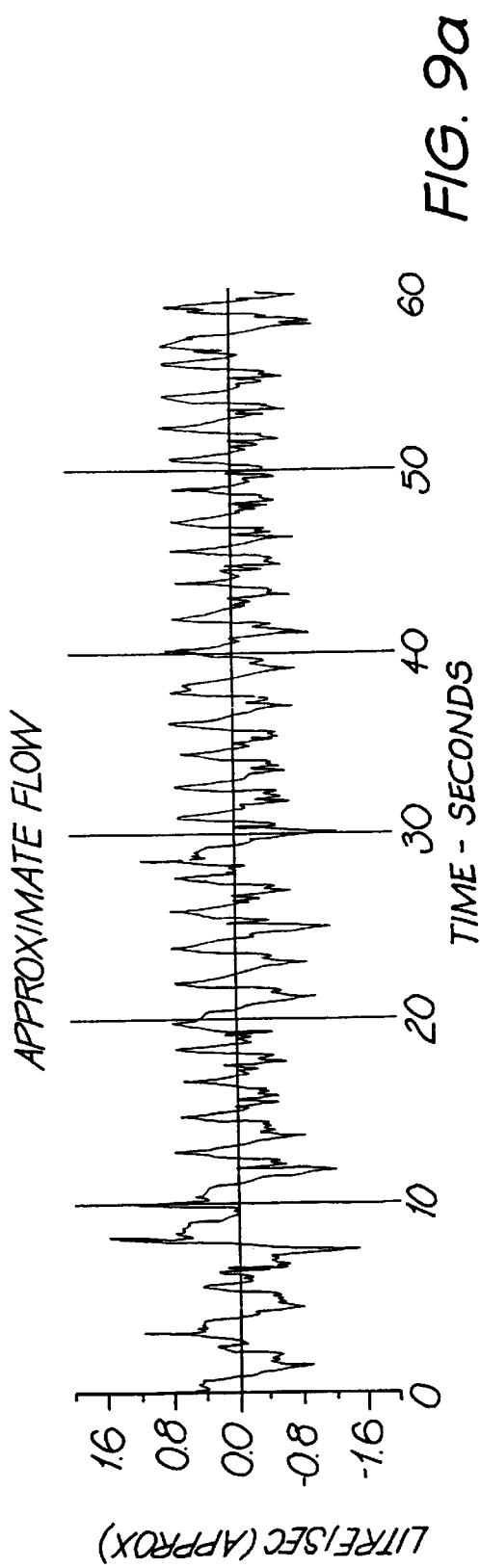
Figure 9B:
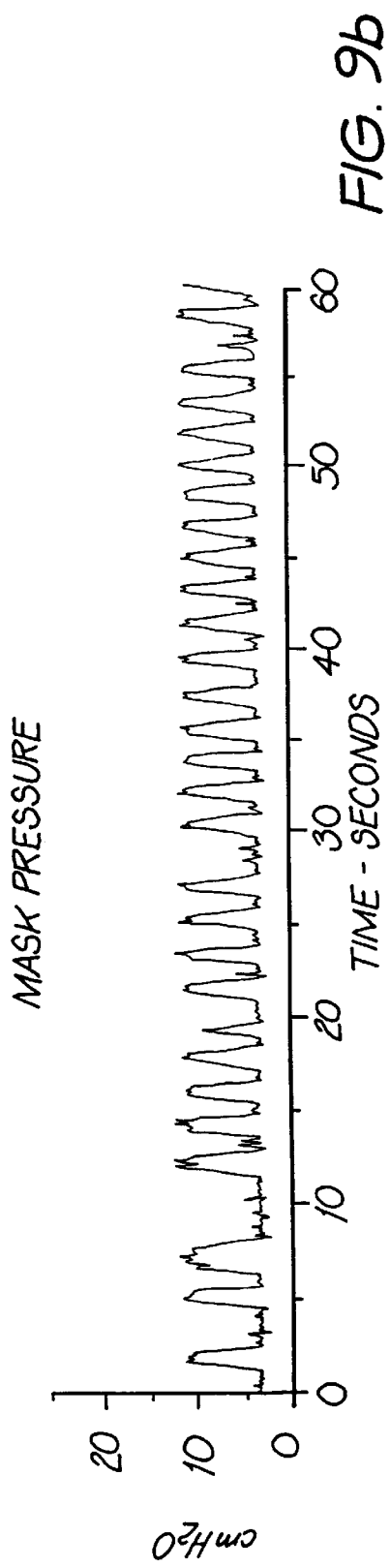

FIGS. 8a–9b relate to a separate patient suffering severe lung disease. FIGS. 8a and 8b show the event of the maximum IPAP duration being defeated with the subsequent immediate asynchronous nature of the patient's respiration. The traces of FIGS. 9a and 9b show an example of respiration and treatment pressure showing a high degree of synchronism with maximum IPAP duration in effect.

Figure 10:
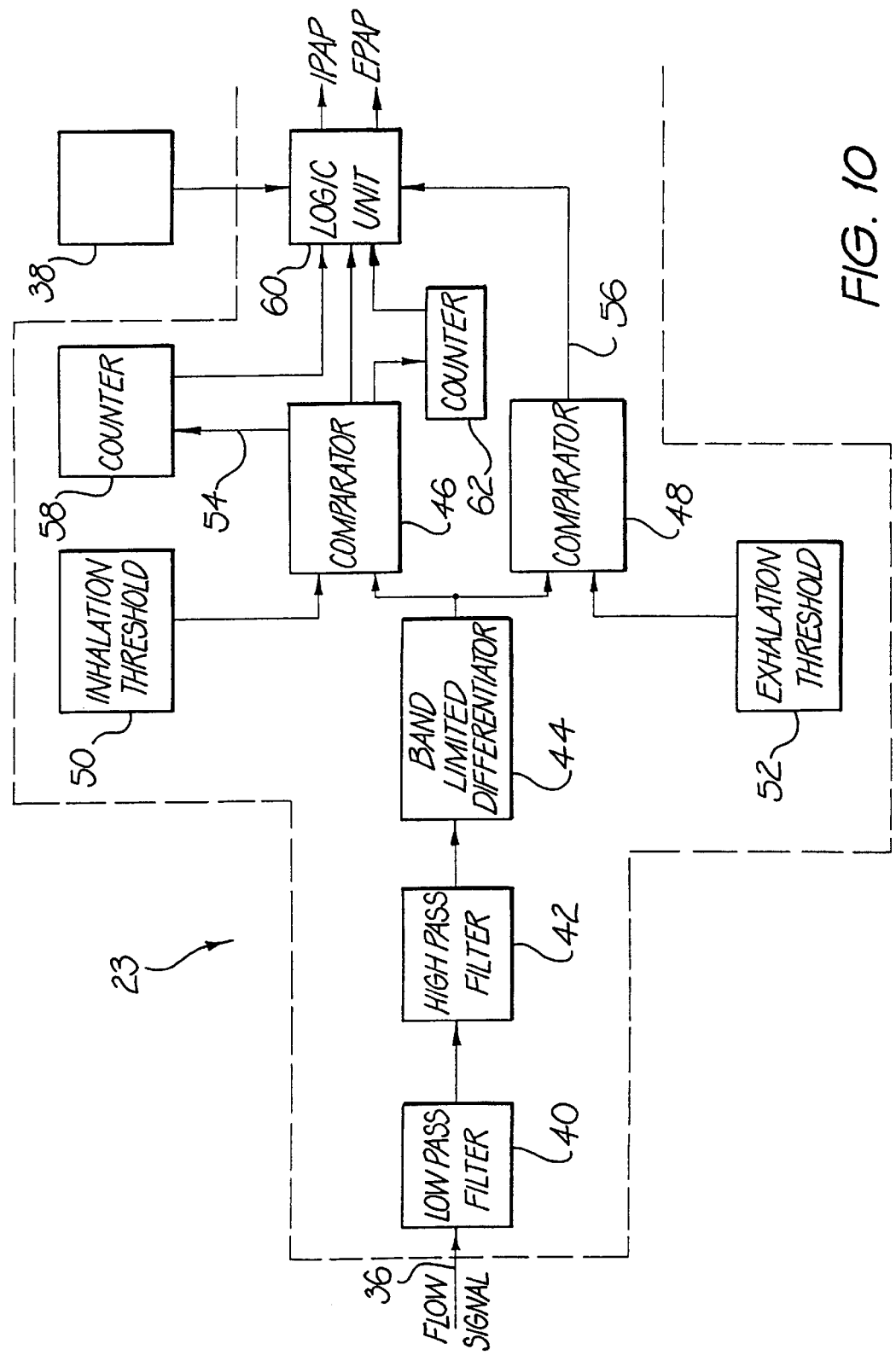
FIG. 10 is a functional block diagram of a respiration detection circuit incorporating a variable minimum IPAP duration.

FIG. 10 is a slightly modified form of the arrangement shown in FIG. 2, in that the output from the comparator 46, indicative of a transition to inspiration (the commencement of inspiration) also is provided to the logic unit 60. Furthermore, a second counter 62 is provided, also receiving the output from the comparator 46 and, in turn, its output being provided to the logic unit 60. The counter 62 is free-running, in the sense that it is not resettable in the absence of continuing inspiration, manifested by a negative gradient in the flow signal. The controls 38 also include the facility for selecting the minimum IPAP duration, which is provided to the logic unit 60. The minimum duration typically will be set at 300 ms, meaning that following sensing of commencement of inspiration, even if the output of the comparator 46 changes in response to detect a change to expiration, the IPAP state will be forced by the logic unit 60 until expiration of the 300 ms minimum duration determined from the counter 62. Thus the logic unit 60 gives precedence to the signal provided by the second counter 62 ignoring any resetting of the first counter 58 until the minimum duration has elapsed.

The embodiment shown in FIG. 10 thus provides the function of having a selectable minimum IPAP duration following detection of commencement of inspiration regardless of any sensed change to expiration, and has a maximum duration/time-out that forces a change to EPAP treatment in the absence of any earlier sensed change of state to expiration. The counter 62 is automatically reset when it reaches its maximum value.

Figure 11:
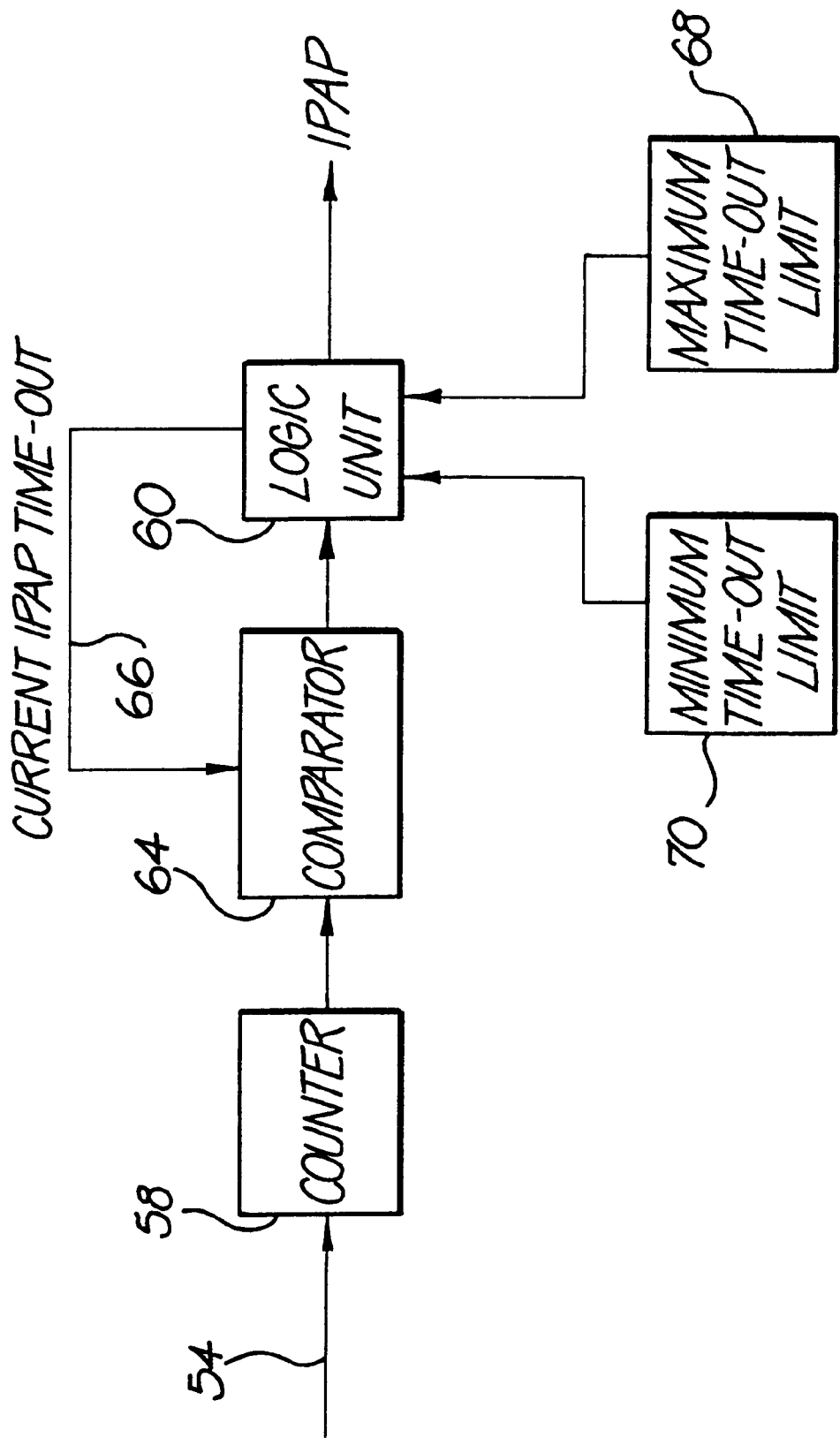
FIG. 11 is a functional block diagram showing automatic adjustment of IPAP duration.

FIG. 11 shows an arrangement for the automatic adjustment of the maximum IPAP duration/time-out that is a modification of the arrangement shown in FIG. 10. In this way, the time-out period can automatically adjust to account for variations in a patient's breathing. The output from the resettable counter 58 is provided to a further comparator 64. The counter 58 has the same role as before in counting time since the last transition to inspiration. The signal 66 fed-back from the logic unit 60 to the comparator 64 represents the "current IPAP time-out" value, and this is compared with the counter value by the comparator 64. The output from the comparator 64 will change state when the current IPAP time-out value elapses and there has been no detection of a transition to expiration, in which case there will be an incremental increase of the current IPAP time out towards the maximum time-out limit specified by the relevant storage unit 68. In the event that the counter 58 times-out in advance of the current IPAP time-out value, then the logic unit 60 will attempt to adapt the current IPAP time-out value by way of reduction in an incremental manner towards the minimum time-out limit set by the relevant storage unit 70. Indicative minimum and maximum time-out limits are 300 ms and 3 seconds. The maximum and minimum time-out limits held by the respective storage units 68,70 can be set by the physician using a potentiometer or other input means. Alternatively, default values can be used. In this manner, the current IPAP time-out value will be continuously updated to be close to the patient's prevailing inspiratory time, so that if the transition to inspiration is not detected or triggered for whatever reason, the time-out period will be closest to the normal period, and so a change to EPAP treatment pressure will result still substantially in synchronism with the patient's respiration.

Clearly, one, two or all of the embodiments can be implemented for the control of CPAP or assisted respiration apparatus and fall within the broad scope of the present invention.

What is claimed is:

1. A controller for a flow generator to supply breathable gas cyclically at an inspiration pressure and at an expiration pressure substantially in synchronism with a patient's respiration, the controller comprising:
    (a) a data processor for receiving an input respiration flow signal and for detecting transitions between inspiration and expiration from said flow signal to discriminate between patient inspiration and expiration, and for outputting a control signal to the flow generator to set the inspiration pressure and the expiration pressure;
    (b) a first timer to manually adjust or select a first time duration commencing from the last transition to inspiration, whereby if said first time duration elapses before the data processor detects a transition to expiration by the patient, the output signal from the data processor causes the flow generator to supply said expiration pressure; and
    (c) a second timer to manually adjust or select a second time duration, shorter than or equal to said first time duration, commencing from said last transition to inspiration corresponding to the data processor forcing said flow generator to supply said inspiration pressure until said second time duration elapses even if during said second time duration there is a transition to expiration by the patient.

2. A controller as claimed in claim 1, wherein said first timer is constructed and arranged so as not to be adjustable by the patient.

3. A controller as claimed in claim 1, wherein said data processor periodically updates said first time duration based on one or more subsequent respiratory transitions to expiration and whether the first time duration elapses before one or more of said subsequent transitions occur to converge the elapse of said first time duration with said subsequent transitions to expiration.

4. The controller as claimed in claim 1, wherein said data processor differentiates said respiratory flow signal, the polarity of the differentiated signal representing either inspiration or expiration.

5. A controller as claimed in claim 1, wherein said second timer is patient adjustable with respect to said second time durations.

6. A flow generator for supplying breathable gas cyclically at an inspiration pressure and an expiration pressure substantially in synchronism with the patient's respiration, the flow generator comprising:
    a turbine to pressurize inlet breathable gas;
    a variable speed electric motor to control operation of said turbine and thus the pressure of breathable gas delivered by the turbine; and
    a controller comprising:
        (a) a data processor for receiving an input respiration flow signal and for detecting transitions between inspiration and expiration from said flow signal to discriminate between patient inspiration and expiration, and for outputting a control signal to the flow generator to set the inspiration pressure and the expiration pressure;
        (b) a first timer to manually adjust or select a first time duration commencing from the last transition to inspiration, whereby if said first time duration elapses before the data processor detects a transition to expiration by the patient, the output signal from the data processor causes the flow generator to supply said expiration pressure; and
        (c) a second timer to manually adjust or select a second time duration, shorter than or equal to said first time duration, commencing from said last transition to inspiration corresponding to the data processor forcing supply of inspiration pressure until said second time duration elapses even if during said second time duration there is a transition to expiration by the patient.

7. The flow generator of claim 6, further comprising a housing within which are located said turbine, said electric motor and said controller, and further wherein said first timer includes a control device by which said first time duration can be set, the control device being constructed and arranged so as to not be adjusted by a patient.

8. A method for controlling the supply of breathable gas to a patient cyclically at an inspiration pressure and at a lower expiration pressure substantially in synchronism with the patient's respiration, the method comprising:
    (a) measuring patient respiratory flow;
    (b) detecting transitions between inspiration and expiration from said respiratory flow to discriminate between patient inspiration and expiration;
    (c) controlling the pressure of gas to be at the inspiration pressure during patient inspiration and at the expiratory pressure during patient expiration;
    (d) prescribing a first time duration commencing from the last transition to inspiration by the patient, and if said duration elapses before patient transition to expiration, causing the pressure of gas to be at the expiratory pressure; and
    (e) prescribing a second time duration commencing from the last transition to inspiration, shorter than or equal to said first time duration, and causing the pressure of gas to be at the inspiratory pressure until the elapse of said second time duration even if there is a transition to expiration by the patient during the second time duration.

9. A method as claimed in claim 8, further comprising:
    (f) updating said first time duration based on one or more subsequent respiratory transitions to expiration and whether the first time duration elapses before one or more of said subsequent transitions occur to converge the elapse of said first time duration with said subsequent transitions to expiration.

10. A method as claimed in claim 9, wherein step (b) further comprises differentiating a signal of said respiratory flow, the polarity of the differentiated signal representing either inspiration or expiration.

11. An apparatus for the supply of breathable gas cyclically at an inspiratory pressure and an expiration pressure substantially in synchronism with the patient's respiration, the apparatus comprising:

a turbine to pressurize inlet breathable gas;

a variable speed electric motor to control operation of said turbine and thus the pressure of breathable gas delivered by the turbine;

a gas delivery system coupled to the turbine and providing said breathable gas to the patient's airway;

a flow sensor located in said gas delivery system to provide a respiration flow signal therefrom; and a controller comprising:

(a) a data processor for receiving said respiration flow signal and for detecting transitions between inspiration and expiration from said flow signal to discriminate between patient inspiration and expiration, and for outputting a control signal provided to the motor to set the inspiration pressure and the expiration pressure;

(b) a first timer to manually adjust or select a first time duration commencing from the last transition to inspiration, whereby if said first time duration elapses before the data processor detects a transition to expiration by the patient, the output signal from the data processor causes the flow generator to supply said expiration pressure; and (c) a second timer to manually adjust or select a second time duration, shorter than or equal to said first time duration, commencing from said last transition to inspiration corresponding to the data processor forcing said flow generator to supply said inspiration pressure until said second time duration elapses even if during said second duration there is a transition to expiration by the patient.

12. The apparatus as claimed in claim 11, wherein said gas delivery system comprises a nose mask coupled to a flexible conduit.

13. The apparatus of claim 11, further comprising a housing within which are located said turbine, said electric motor and said controller, and further wherein said first timer includes a control device by which said first time duration can be set, the control device being constructed and arranged so as to not be adjusted by a patient.

14. The apparatus as claimed in claim 11, wherein said gas delivery system comprises a face mask coupled to a flexible conduit.

15. The apparatus as claimed in claim 11, wherein said first timer is constructed and arranged so as not to be adjustable by the patient.

16. The apparatus as claimed in claim 11, wherein said data processor periodically updates said first time duration based on one or more subsequent respiratory transitions to expiration and whether the first time duration elapses before one or more of said subsequent transitions occur to converge the elapse of said first time duration with said subsequent transitions to expiration.

17. The apparatus as claimed in claim 11, wherein said data processor differentiates said respiratory flow signal, the polarity of the differentiated signal representing either inspiration or expiration.

* * * * *